US00PP28259P3

(12) United States Plant Patent
Van Dijk

(10) Patent No.: US PP28,259 P3
(45) Date of Patent: Aug. 8, 2017

(54) ***ANTHURIUM* PLANT NAMED 'ANTHDOTFAN'**

(50) Latin Name: ***Anthurium andreanum* L.**
Varietal Denomination: ANTHDOTFAN

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 102 days.

(21) Appl. No.: 14/757,198

(22) Filed: Dec. 3, 2015

(65) Prior Publication Data

US 2017/0164542 P1 Jun. 8, 2017

(51) Int. Cl.
*A01H 5/02* (2006.01)

(52) U.S. Cl.
USPC ..... Plt./369

(58) Field of Classification Search
USPC ..... Plt./369
See application file for complete search history.

(56) References Cited

PUBLICATIONS

UPOV hit on *Anthurium* named 'Anthdotfan', QZ PBR41016, published Feb. 15, 2014.*

* cited by examiner

*Primary Examiner* — Anne Grunberg
(74) *Attorney, Agent, or Firm* — Jondle & Associates, P.C.

(57) ABSTRACT

A new and distinct variety of *Anthurium* plant named 'ANTHDOTFAN' particularly distinguished by having red, cordate and very durable spathes that retain the original color for a very long period of time, brown and cordate, durable leaves, pinkish cataphylls, reddish brown peduncles, rich flowering continuously throughout the year and a plant height of 30 cm to 35 cm, is disclosed.

4 Drawing Sheets

Genus and species: *Anthurium andreanum* L.
Variety denomination: 'ANTHDOTFAN'.

BACKGROUND OF THE NEW PLANT

The present invention comprises a new and distinct variety of *Anthurium*, botanically known as *Anthurium andreanum* L., and hereinafter referred to by the variety name 'ANTHDOTFAN'. The new variety originated from a hybridization made in September 2006 in Bleiswijk, The Netherlands. The female parent was a dark red *Anthurium* pot plant designated '9842-01' (unpatented), and the male parent was a red *Anthurium* plant designated '9632-01' (unpatented).

A single plant was selected in November 2008 and has been asexually reproduced repeatedly by tissue culture in Bleiswijk, The Netherlands over a seven-year period. The present invention has been found to retain its distinctive characteristics through successive asexual propagations.

Plant Breeder's Rights for this variety have been applied for in the European Union on Nov. 18, 2013. 'ANTHDOTFAN' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Red, cordate spathe;
2) White spadix with yellow tip;
3) Brown cordate leaves;
4) Reddish-brown peduncle; and
5) Pinkish cataphyll.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 40-week old plant grown in a greenhouse in Bleiswijk, The Netherlands in August 2015.

DESCRIPTION OF THE NEW VARIETY

Figure 1:
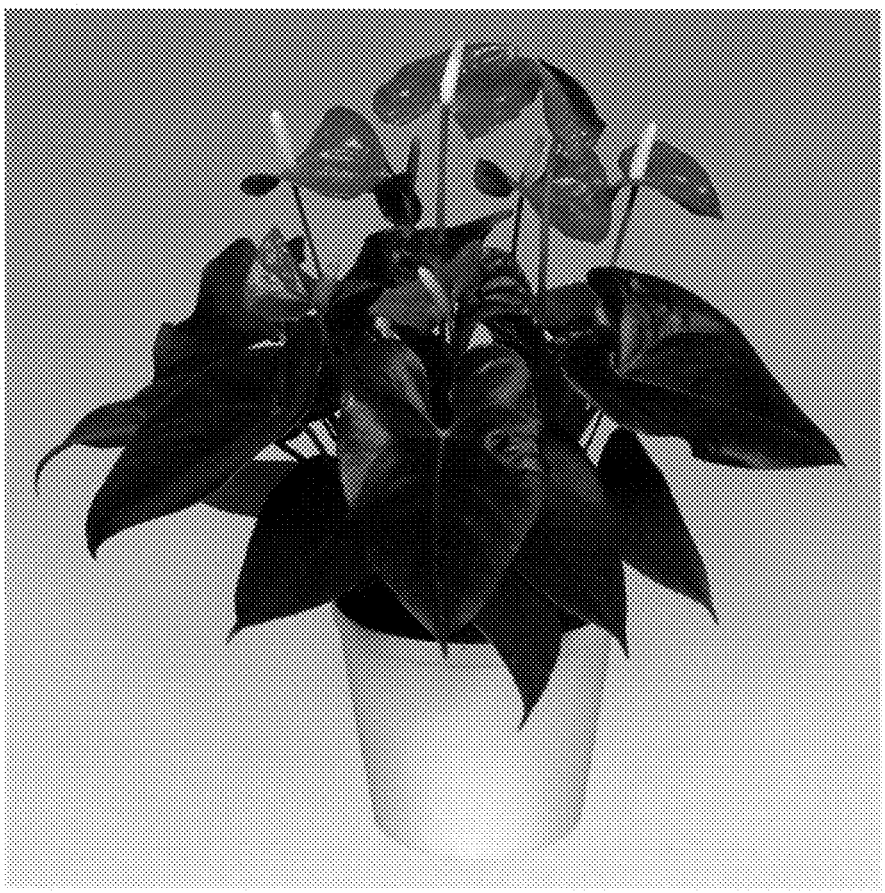
FIG. 1 shows the overall plant habit, including blooms and foliage.
Figure 2:
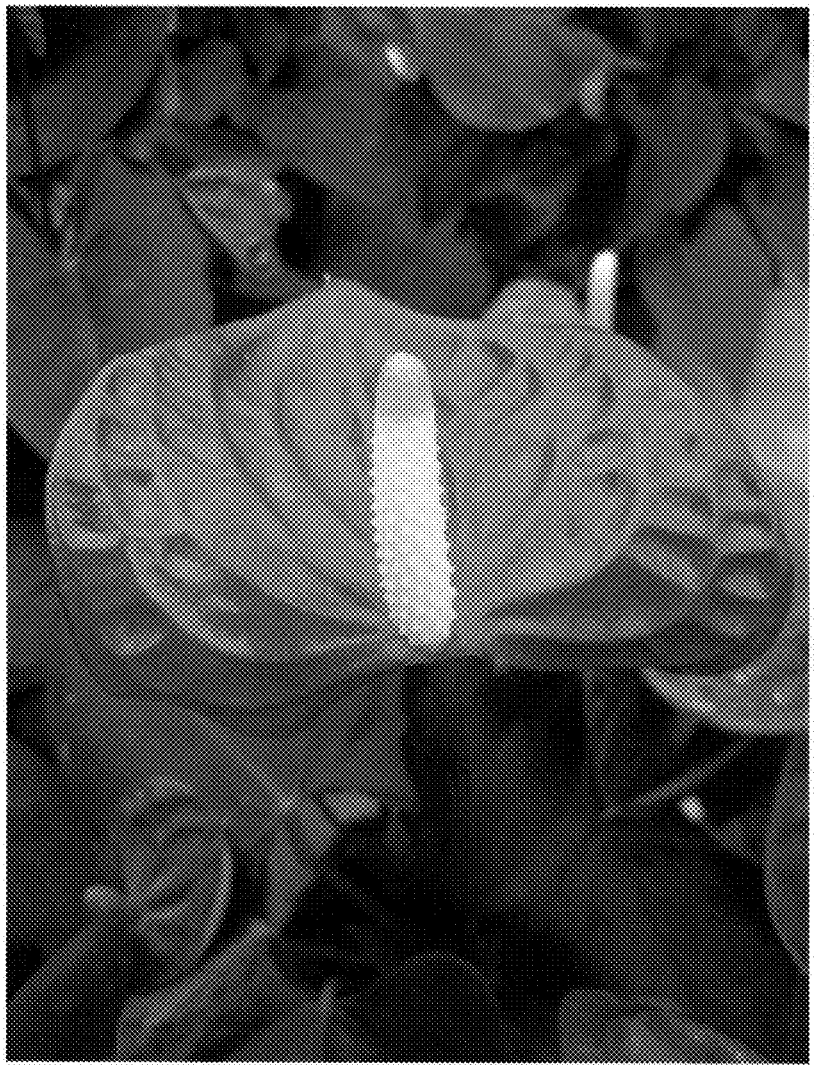
FIG. 2 shows a close-up of the mature spathe.
Figure 3:
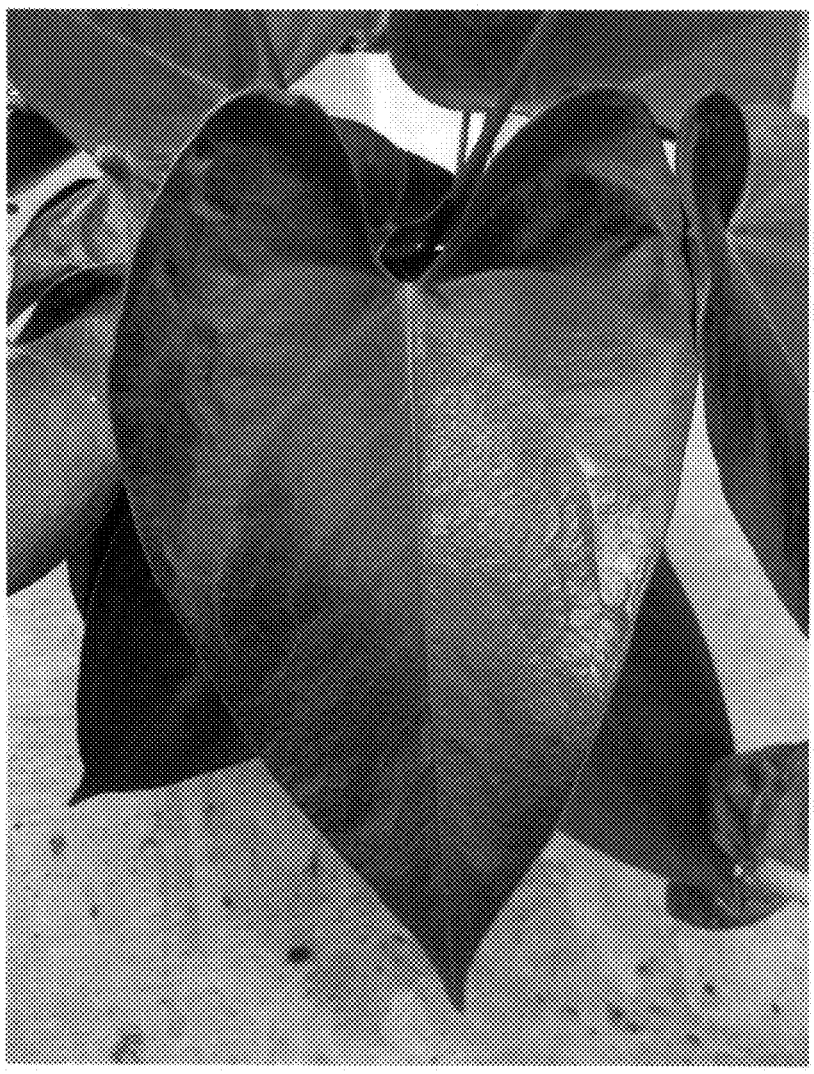
FIG. 3 shows a close-up of the upper immature leaf blade surface.
Figure 4:
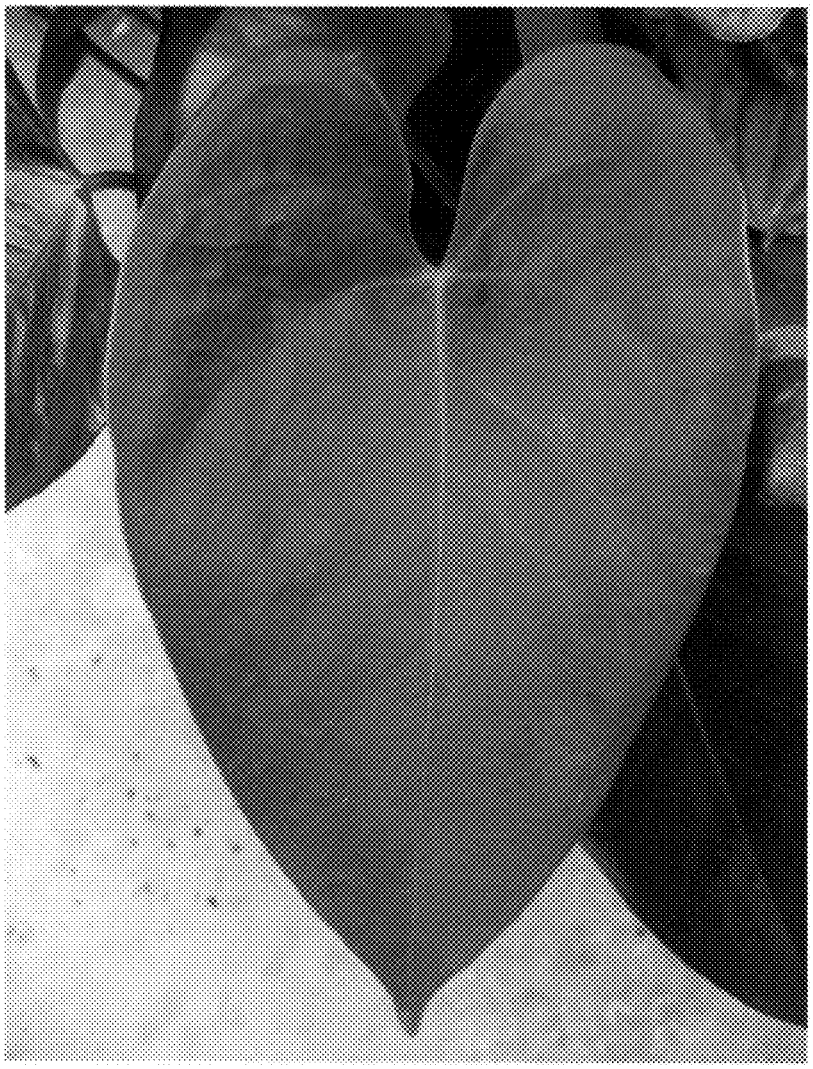
FIG. 4 shows a close-up of the upper mature leaf blade surface.

The following detailed description sets forth the distinctive characteristics of 'ANTHDOTFAN'. The data which define these characteristics were collected from asexual reproductions carried out in Bleiswijk, The Netherlands. The plant history was taken on 40-week old plants which were planted from tissue culture in 14-centimeter pots and grown in a glass greenhouse between 19° C. and 24° C. Observations were made in August 2015. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family.*—Araceae.

*Botanical.*—*Anthurium andreanum* L.

*Common name.*—*Anthurium.*

*Demonimation.*—'ANTHDOTFAN'.

Parentage:

*Female parent.*—*Anthurium* plant '9842-01' (unpatented).

*Male parent.*—*Anthurium* plant '9632-01' (unpatented).

Plant:

*Propagation.*—Tissue culture.

*Root description.*—Fleshy-white/orange colored roots with small hairy lateral roots having yellow-colored root tips.

*Time to produce a finished flowering plant.*—35 to 40 weeks for a 14 cm pot.

*Growth habit.*—Herbaceous perennial.

*Height (measured from soil, including inflorescence).*—30.0 cm to 35.0 cm.

*Width (measured from leaf tips).*—40.0 cm to 45.0 cm.

Leaves:

*Immature leaves.*—Length: 12.0 cm to 18.0 cm. Width: 8.0 cm to 12.0 cm. Color: Upper surface: RHS 200A. Lower surface: RHS 177A. Texture (both upper and lower surfaces): Shiny.

*Mature leaves.*—Length (fully expanded): 12.0 cm to 18.0 cm. Width: 8.0 cm to 12.0 cm. Shape: Ovate-cordate. Apex: Acuminate. Base: Cordate. Leaf blade angle with the petiole: Between 120 degrees and 130 degrees. Leaf margin: Entire. Color: Upper surface: RHS NN137A. Lower surface: RHS NN137B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 146C.

*Lobes.*—Arrangement: Leaf blade has two lobes extending past the petiole. The lobes are non-touching. Length of lobes of mature leaf blades: 2.0 cm to 3.0 cm. Width of lobes of mature leaf blades: 4.0 cm to 5.0 cm. Distance for petiole/leaf junction to highest point on lobes of mature leaf blades: 1.5 cm to 2.5 cm.

*Petiole.*—Cross-section: Round. Diameter: 0.2 cm to 0.3 cm. Length: 9.0 cm to 12.0 cm for a mature leaf size. Color: Mature leaf: RHS 144A. Immature leaf: RHS 165A. Cataphyll color surrounding the petiole: Outside: RHS 181C. Inside: RHS 181D.

*Geniculum.*—Length: 1.5 cm to 2.0 cm. Width: 0.25 cm to 0.35 cm. Color: RHS 144A.

Inflorescence:

*Arrangement.*—Single.

*Flowering habit (length of flowering season).*—Continuous.

*Number of inflorescences per plant.*—5 to 7.

*Fragrance.*—Absent.

*Longevity of inflorescence on plant.*—Over a year.

*Longevity of inflorescence when cut.*—35 to 40 days.

Spathe:

*Buds.*—The spathe is tightly rolled around the spadix and extrudes from the peduncle sheath. After the spathe is fully open the peduncle elongates some extra centimeters.

*Arrangement.*—Spathe angle with the peduncle is between 90 degrees and 100 degrees; the spathe stands on a wiry peduncle about 4.0 cm to 10.0 cm above the foliage.

*Shape.*—Cordate.

*Apex.*—Mucronate.

*Base.*—Cordate.

*Texture.*—Shiny and blistered.

*Margin.*—Entire.

*Size.*—Length: 5.0 cm to 11.0 cm. Width: 5.0 cm to 10.0 cm.

*Lobes.*—Arrangement: The spathe has two lobes extending past the peduncle. The lobes are non-touching. Length: 1.0 cm to 2.5 cm. Width: 2.5 cm to 4.5 cm.

*Color.*—Just fully open: Upper surface: RHS 53A. Lower surface: RHS N45A. This red color remains for a very long period, at least more than 30 weeks after opening.

Peduncle:

*Shape.*—Erect.

*Cross-section.*—Round.

*Length.*—15.0 cm to 25.0 cm.

*Diameter.*—0.2 cm to 0.3 cm.

*Color.*—RHS 165A.

Flowering time:

*General.*—One small rooted untreated tissue culture plant of 8.0 cm tall will flower after 8 to 9 months, depending on the season, and 4 to 6 blossoms appear. More blossoms appear after some additional weeks so that a full flowering and commercial plant will have 6 to 8 red spathes. Smaller blossoms may occur on less mature plants.

Spadix:

*Size.*—Length: 2.0 cm to 3.5 cm (depending on flower size). Width (at apex): 0.35 cm to 0.45 cm. Width (at base): 0.5 cm to 0.6 cm.

*Shape.*—Columnar.

*Angle from spadix tip to peduncle.*—160 to 180 degrees.

*Texture.*—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color.*—Immature: RHS 12B. Mature: RHS 8A. Aged: RHS 144A.

Flowers:

*Quantity per spadix.*—150 to 200.

*Spadix flower arrangement.*—Bisexual, rounded in cross-section.

*Shape.*—Rounded.

*Size.*—Length: 0.05 cm to 0.1 cm. Diameter (maximum): 0.1 cm.

*Color.*—RHS 8A.

Reproductive organs:

*Stamens.*—Not visible.

*Pollen amount.*—Very few.

*Pollen color.*—RHS 156D.
*Pistil.*—Quantity: Many. Length: Less than 0.01 cm. Color: RHS 156D.
*Style.*—Not observed.
*Stigma.*—Shape: Ovoid. Diameter: Less than 0.01 cm. Color: RHS 156D.
*Ovary.*—Rarely visible.
*Ovary color.*—Not measured.
Fruit and seed set: None observed.

COMPARISON WITH PARENTAL AND COMMERCIAL VARIETIES

'ANTHDOTFAN' differs from the female parent plant '9842-01' (unpatented) in that 'ANTHDOTFAN' has red spathes, whereas '9842-01' has dark red spathes.

'ANTHDOTFAN' differs from male parent plant '9632-01' (unpatented) in that 'ANTHDOTFAN' has brown leaves, whereas '9632-01' has green leaves.

'ANTHDOTFAN' differs from commercial variety 'ANTHCRAXIQ' (unpatented) in that 'ANTHDOTFAN' has a red spathe, whereas 'ANTHCRAXIQ' has an orange spathe. Additionally, 'ANTHDOTFAN' has reddish-brown peduncles, whereas 'ANTHCRAXIQ' has brownish-green peduncles.

'ANTHDOTFAN' differs from commercial variety 'ANTHEPEDI' (U.S. Plant Pat. No. 18,644) in that 'ANTHDOTFAN' has reddish-brown peduncles, whereas 'ANTHEPEDI' has green peduncles. Additionally, 'ANTHDOTFAN' has brown leaves whereas 'ANTHEPEDI' has green leaves.

I claim:

1. A new and distinct variety of *Anthurium* plant named 'ANTHDOTFAN', substantially as illustrated and described herein.

* * * * *